United States Patent
Snyder

(10) Patent No.: US 10,369,039 B1
(45) Date of Patent: Aug. 6, 2019

(54) NASAL DILATOR

(71) Applicant: TRU-BREATHE, INC., Leawood, KS (US)

(72) Inventor: Raymond F. Snyder, Leawood, KS (US)

(73) Assignee: TRU-BREATHE, INC., Leawood, KS (US)

( * ) Notice: Subject to any disclaimer, the term of this patent is extended or adjusted under 35 U.S.C. 154(b) by 0 days.

(21) Appl. No.: 15/240,003

(22) Filed: Aug. 18, 2016

Related U.S. Application Data

(60) Provisional application No. 62/206,624, filed on Aug. 18, 2015.

(51) Int. Cl.
| | | |
|---|---|---|
| *A61F 5/08* | (2006.01) | |
| *A61F 5/56* | (2006.01) | |
| *A61B 5/083* | (2006.01) | |
| *A61B 5/00* | (2006.01) | |
| *A61B 5/08* | (2006.01) | |

(52) U.S. Cl.
CPC .............. *A61F 5/08* (2013.01); *A61B 5/0022* (2013.01); *A61B 5/082* (2013.01); *A61B 5/083* (2013.01); *A61B 5/6819* (2013.01); *A61F 5/56* (2013.01)

(58) Field of Classification Search
CPC ........... A61F 5/08; A61F 5/56; A61M 15/085; A62B 23/06
USPC ................................. 606/199; D24/133, 135
See application file for complete search history.

(56) References Cited

U.S. PATENT DOCUMENTS

| | | | | |
|---|---|---|---|---|
| 6,270,512 B1* | 8/2001 | Rittmann | .................. | A61F 5/08 128/207.18 |
| 2009/0205642 A1* | 8/2009 | McDevitt | .................. | A61F 5/08 128/200.24 |
| 2013/0081637 A1* | 4/2013 | Foley | ........................ | A61F 5/56 128/848 |
| 2013/0144325 A1* | 6/2013 | Allegra | ..................... | A61F 5/08 606/199 |
| 2014/0371776 A1* | 12/2014 | Moya Vicente | .......... | A61F 5/08 606/198 |

OTHER PUBLICATIONS

Breathe Right Nasal Strips, https://www.breatheright.com, accessed Jul. 13, 2016, Applicant Admitted Prior Art.

* cited by examiner

*Primary Examiner* — Diane D Yabut
*Assistant Examiner* — Majid Jamialahmadi
(74) *Attorney, Agent, or Firm* — Lathrop Gage L.L.P.

(57) ABSTRACT

Embodiments of nasal dilators are disclosed. In one embodiment, a nasal dilator has an internal portion with first and second nostril separators and an external portion forming a connection member. Each nostril separator has a generally "C" configuration and includes a first and second end separated by a linking member. The first and second ends have a gap therebetween. The connection member has a generally "U "configuration, and is fixed to the linking members of the first and second nostril separators to form the nasal dilator.

20 Claims, 6 Drawing Sheets

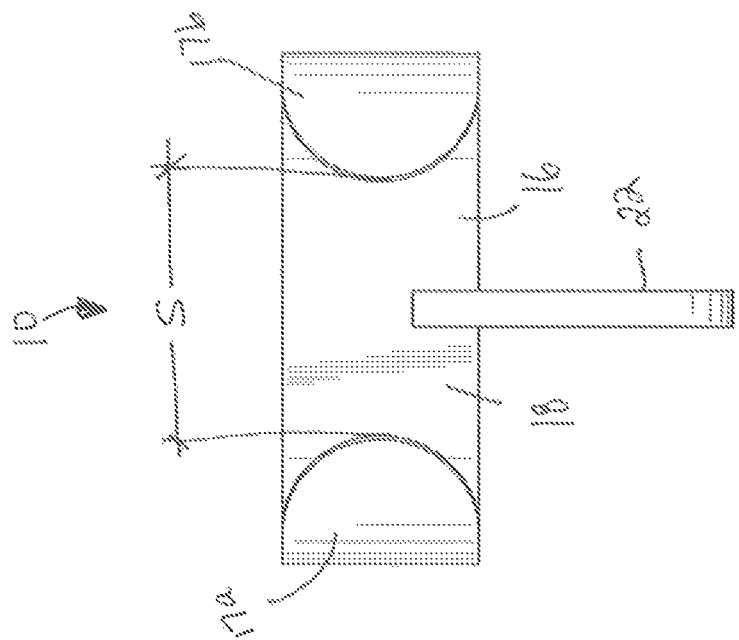
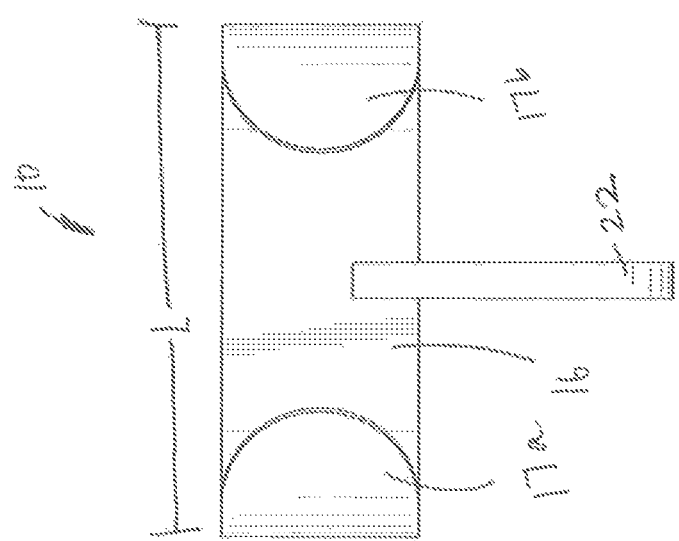

NASAL DILATOR

RELATED APPLICATIONS

This application claims priority to U.S. Provisional Application No. 62/206,624, titled Nasal Dilator, filed on Aug. 18, 2015, the disclosure of which is incorporated herein by reference in its entirety.

BACKGROUND

Oxygen is essential for life. In humans, oxygen plays a vital role in the breathing process and in the metabolism of living organisms. When oxygen is no longer being received into the body, death occurs. However, even slight reductions in oxygen intake can have significant impacts on the body. Decreased oxygen supply to the brain can cause mental performance to wane; however, increasing oxygen supply may improve alertness, reflexes, and memory, and may aid in the treatment of various neurocognitive disorders such as Alzheimer's disease, Parkinson's disease, motor neuron disease, etc.

There are a number of reasons that a person may experience decreased levels of oxygen. In some instances, there is a medical explanation (e.g., blood clots in the lungs) that contributes to an individual's inability to maintain the desired level of oxygen. In other instances, loss of oxygen is due to the person's physical location. For example, those at high altitudes are known to have lower oxygen levels than those at lower altitudes, especially in persons that are over 50 years of age. One affliction affecting nearly 30% of all adults is snoring. Snoring is the result of obstructed air movement during breathing, usually while sleeping. While there are several known or suspected causes of snoring, often more concerning is the correlation between a person's snoring and other health concerns, such as daytime drowsiness, irritability, increased risk of heart attack and stroke, and sleep apnea to name a few.

Varying treatments exist for treating low oxygen levels, ranging from providing a person with pure oxygen to dental appliances to arranging a surgery in an attempt to decrease snoring. However, these treatments are often uncomfortable and inconvenient, require long and/or painful recovery times, and/or are not meant to be employed both at night and during the day. Therefore, apparatus to aid in achieving increased levels of oxygen would be beneficial.

SUMMARY

The following presents a simplified summary of the invention in order to provide a basic understanding of some aspects of the invention. This summary is not an extensive overview of the invention. It is not intended to identify critical elements of the invention or to limit the scope of the invention. Its sole purpose is to present some concepts of the invention in a simplified form as a prelude to the more detailed description provided below.

In one embodiment, a nasal dilator has an internal portion with first and second nostril separators and an external portion forming a connection member. Each nostril separator has a generally "C" configuration and includes a first and second end separated by a linking member. The first and second ends have a gap therebetween. The connection member has a generally "U "configuration, and is fixed to the linking members of the first and second nostril separators to form the nasal dilator.

In another embodiment, a nasal dilator has an internal portion with first and second nostril separators and an external portion forming a connection member. Each nostril separator includes a first and second end separated by a linking member. The first and second ends have a gap therebetween. The connection member is fixed to the linking members of the first and second nostril separators to form the nasal dilator.

BRIEF DESCRIPTION OF THE DRAWINGS

FIG. 4 is a right side view of the nasal dilator of FIG. 1.

FIG. 5 is a left side view of the nasal dilator of FIG. 1.

DETAILED DESCRIPTION

Figure 1:
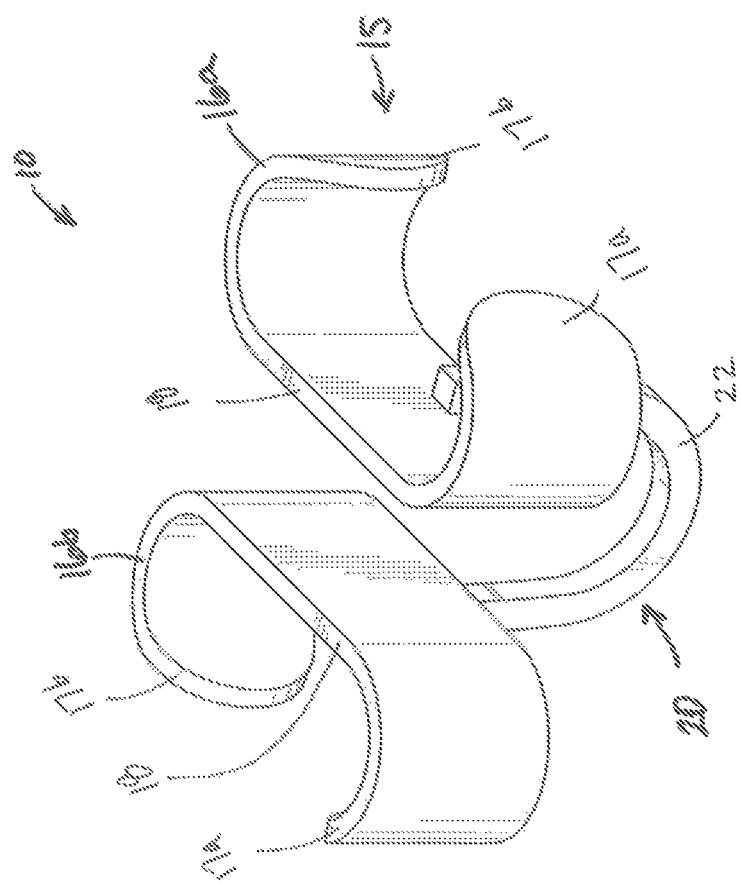
FIG. 1 is a perspective view of a nasal dilator according to one embodiment of the invention.

Disclosed herein are embodiments of a nasal dilator that may be useful for increasing oxygen intake through the nose. Because of the increased flow of air through the nose, use of the nasal dilator may also help with breathing-related ailments such as snoring and sleep apnea.

In one embodiment of the invention, illustrated in FIGS. 1-9, a nasal dilator 10 generally consists of an internal portion 15, which sits inside the nostrils of a patient as described in greater detail below, and an external portion 20.

The internal portion 15 of the nasal dilator 10 may include first and second nostril spreaders 16*a* and 16*b*, respectively. As shown in the figures, the nostril spreaders 16 may be generally "C" shaped and configured to be inserted into respective nostrils of a user. The length and width of the spreaders 16 may be such that the spreaders 16 comfortably open the nostrils of the user.

Because nostril sizes may vary based on the user, it may be desirable to provide various separator sizes (e.g., various lengths and widths). In one embodiment, the separators 16 may be classified into adult small, medium, or large sizes based on the overall length, width, and height of the separators 16. Furthermore, separators 16 may be designed to fit the nostrils of children, and may also be classified into child small, medium, or large sizes.

In one embodiment of the invention, the separators 16 may have a height H ranging from about 3 mm to about 10 mm. The separators 16 may have a width $W_1$ ranging from about 3 mm to about 15 mm. The separators 16 may have a length L ranging from about 10 mm to about 25 mm. As noted above, the separators 16 may generally have a "C" configuration, and thus each separator 16 may have a first end 17*a* and a second end 17*b* connected via a linking member 18, with a space S located between the first and second ends 17*a* and 17*b*. The space S may range from about 3 to 8 mm. A gap G between the separators 16 may range from approximately 2 mm to approximately 8 mm. The separators 16 may further be moldable to a user's specific height, width, and/or length requirements.

In one embodiment, the separators 16 may have varying heights and/or widths. For example, the separator ends 17 may have a first height, and the separator linking member 18 may have a second height, such that the edges of the separators connecting the linking member 18 and the separator ends 17 are angled. Additionally, the separator ends 17a and 17b may or may not have corresponding heights and/or widths.

The external portion 20 of the nasal dilator may comprise a connection member 22 that connects the first and second nostril separators 16a and 16b. The external portion may take a variety of configurations. In one embodiment, the connection member 22 resembles a "U" or "C" shape. In another embodiment (FIG. 9) the connection member 22 has an open triangular. Still another embodiment, the connection member 22 may have an open square configuration. Other configurations of the connection member 22 are also contemplated within the scope of this invention.

Figure 3:
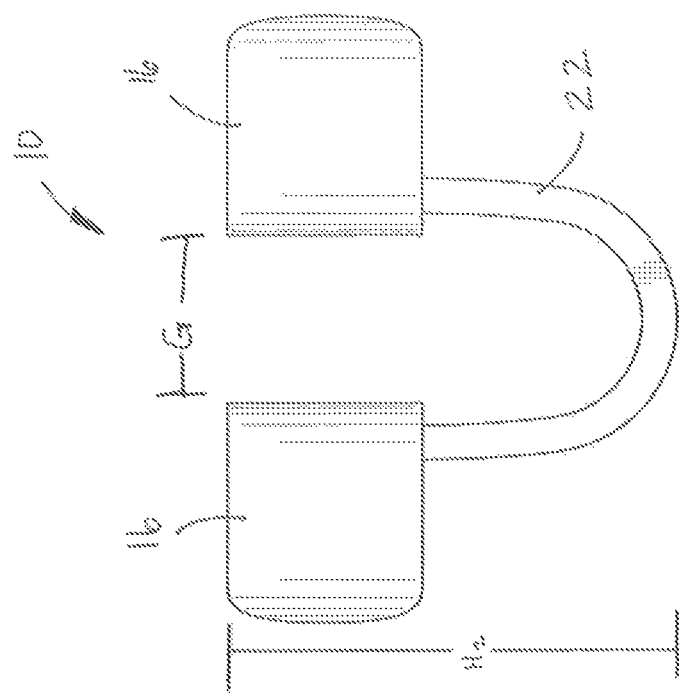
FIG. 3 is a bottom view of the nasal dilator of FIG. 1.
Figure 2:
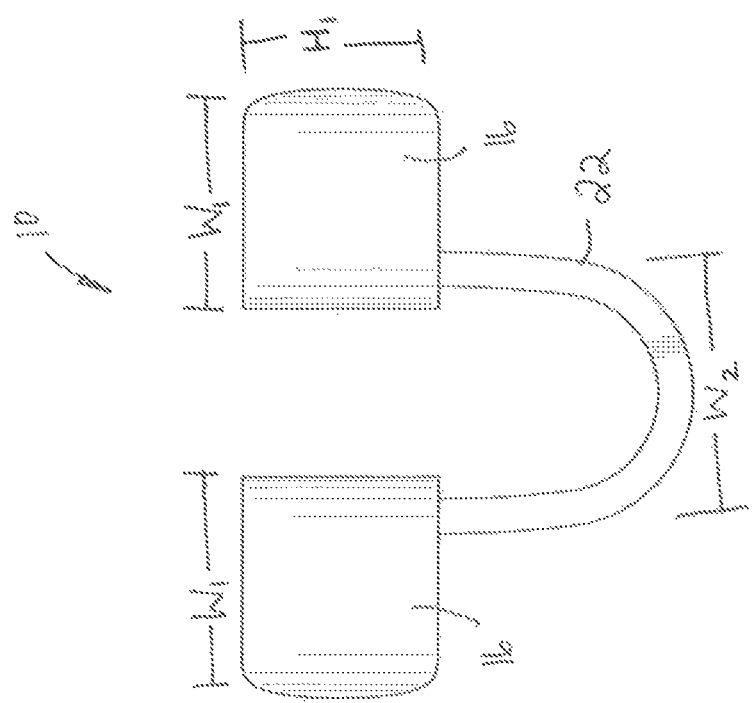
FIG. 2 is a top view of the nasal dilator of FIG. 1.
Figure 6:
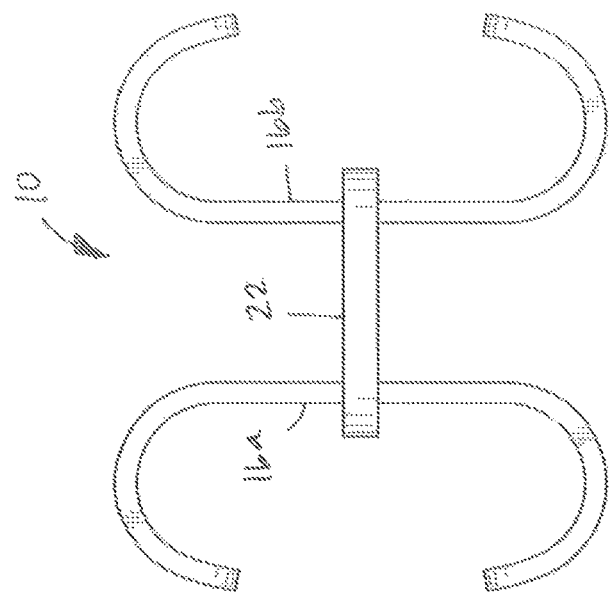
FIG. 6 is a rear view of the nasal dilator of FIG. 1.
Figure 7:
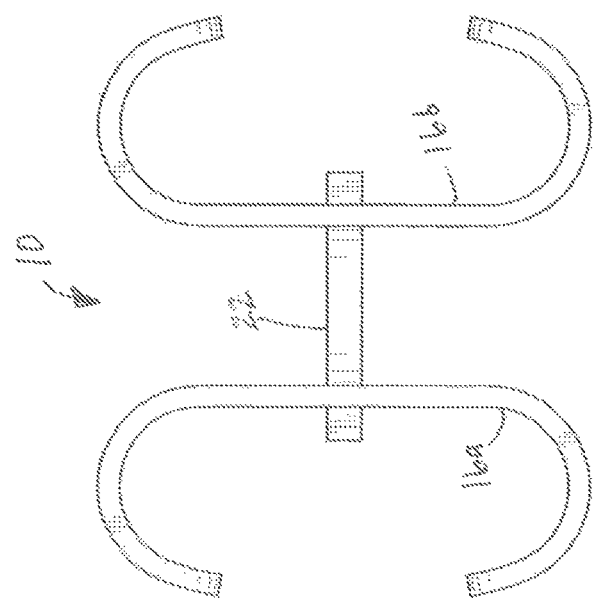
FIG. 7 is a front view of the nasal dilator of FIG. 1.
Figure 9:
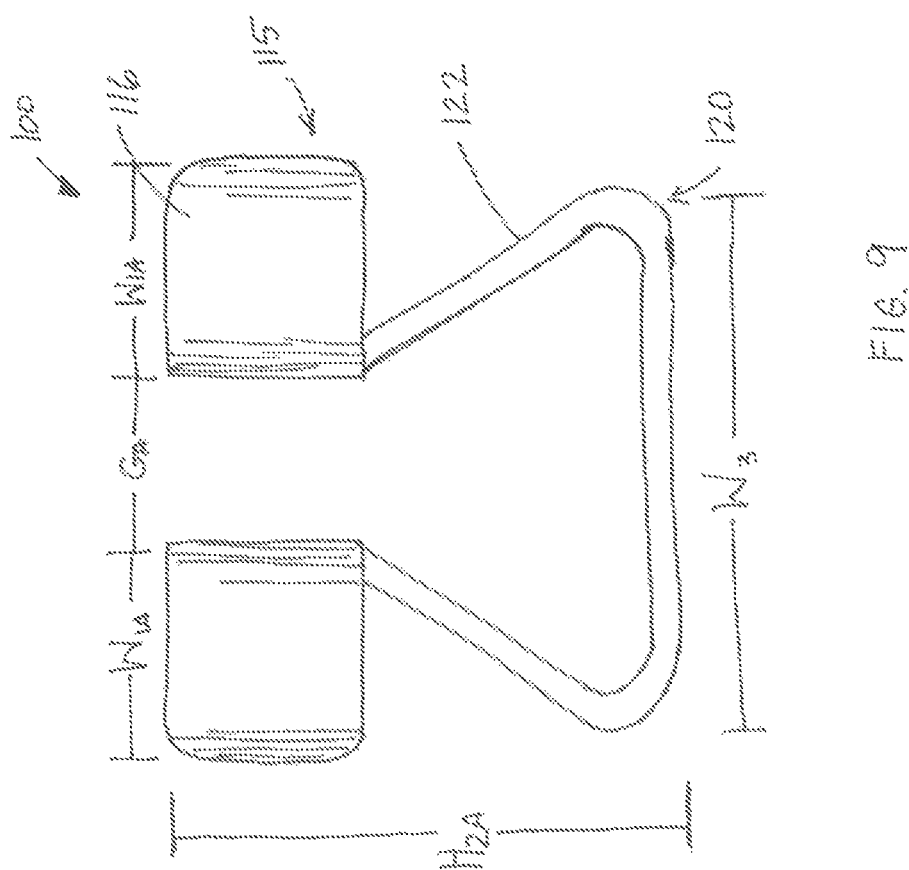
FIG. 9 is a front view of a nasal dilator according to another embodiment of the invention.

The connection member 22 may have a width $W_2$ ranging from approximately 5 mm to approximately 15 mm, depending on the configuration of the connection member 22. For example, FIG. 9 illustrates an alternative embodiment of a nasal dilator 100 that is substantially similar to nasal dilator 10, except as shown and described. Here, the connection member 122 has a width $W_3$ that is substantially equal to the width $W_{1A}$ of separators 116 plus the gap $G_A$. FIGS. 2 and 3 illustrate the nasal dilator 10 having a "U" shaped connection member 22.

The connection member 22, 122 may be flexible to allow a user to adjust the gap G of the dilator for insertion into the nostrils. In one embodiment, the connection member 22, 122 may be adjusted by the user and maintained in the adjusted position. In another embodiment, the connection member 22 may be flexible enough that the separators 16 can be squeezed together for insertion into the nostrils, and the connection member 22 subsequently returns to its original position. In this way, the user can be sure that, even after adjustment for insertion, the nostrils are adequately opened to achieve maximum air flow through the nostrils. The connection member 22, 122 may further be moldable to a user's specific height and/or width requirements. In still another embodiment, the separators 16, 116 may be connected to the connection member 22 via a hinged spring. The spring may bias the separators 16, 116 outwards but still allow for flexibility of the dilator for insertion into the nostrils.

In one embodiment, the separators 16, 116 are welded or otherwise secured to the connection members 22, 122. In another embodiment, the separators 16, 116 may be removable from the connection member 22, 122 such that the user may try different sizes (e.g., of varying height, width, and/or length) of separators 16, 116 until the desired size is found. In still another embodiment, a user may be measured prior to purchase of a nasal dilator 10, 100, the separators 16, 116 thus being customized to the user's requirements. Optionally, the separators 16, 116 may be adjustable on the external portion 22, 122 such that an overall height $H_2$, $H_{2A}$ of the dilator 10, 100 may be increased or decreased as desired.

The design of the dilator 22, 122, and particularly the separators 16, 116, may be such that the dilator 10, 100 does not slip from its position once inserted into the user's nostrils. This ensures that the dilator 10, 100 is both comfortable and effective for the entire length of time that the user may have the dilator 10, 100 in place.

The connection member 22, 122 may be formed from approximately 1 mm square or rounded wire, which may be, for example, stainless steel, silver, titanium or other appropriate metal. The separators 16, 116 may be formed from 20 gauge stainless steel sheet metal or other appropriate metal. Alternatively, one or more portions of the dilator 10, 100 may be formed of an appropriate plastic, such a polypropylene or polyvinyl chloride, or carbon fiber.

It may be desirable to coat the connection member 22, 122 and/or the separators 16, 116 with a coating such as sterling silver, gold, rose gold, et cetera. This may aid in both ensuring that the dilator 10, 100 does not cause an allergic reaction with the wearer's skin and adding aesthetic appeal to the dilator 10, 100.

Figure 8:
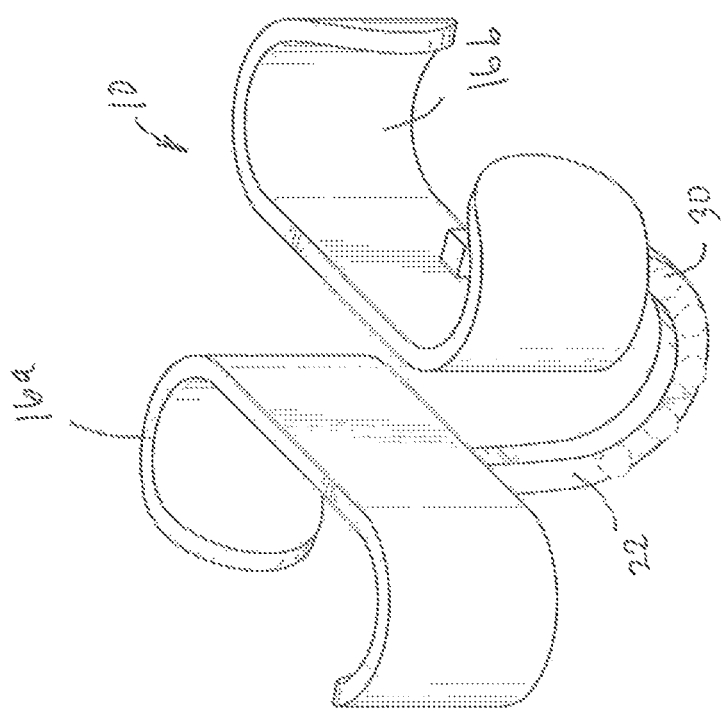
FIG. 8 is a perspective view of a nasal dilator according to another embodiment of the invention.

To encourage use of the dilator 10, 100 throughout the day, the connection member 22, 122 may be equipped with various decorations 30, for example as shown in FIG. 8. In one embodiment, it may be desirable for jewels or charms to be embedded or otherwise secured to the connection member 22, 122. In this way, the dilator 10, 100 may serve both as a beneficial breathing device and a fashion forward piece of nasal jewelry.

When the dilator 10, 100 is positioned such that the separators 16, 116 are inserted into the nostrils, the size of the nostril is increased to allow for increased air exchange to and from the nasal cavity. When the size of the nostril is increased, obstructions inside the nasal cavity may be minimized and respiration may more efficiently proceed. It is estimated that oxygen intake may be increased by as much as 50%.

The nasal dilator may be further equipped with electronic means for measuring the efficiency of nostril and/or mouth air exchange. For example, the dilator 10, 100 may include a sensor for sensing the amount of oxygen entering through the nasal cavity. Alternately (or additionally), the sensor may monitor, for example, $CO_2$ output. Information received from the sensor may be transmitted, for example, over a wireless network, to a computer or other monitoring device. In one embodiment, the information may be transmitted and stored for review by a physician or other care taker.

The nasal dilator 10, 100 may be provided in a sleep system comprising the nasal dilator and an eye mask. In combination, the system may promote a healthy night's sleep. It is known that the presence of light can be a hindrance to sleep. Thus, providing a sleep mask may aid in keeping out unwanted light. And, as described above, the nasal dilator may increase the amount of oxygen taken in by the body when breathing. Together, the sleep system may allow for enhanced sleep, thus allowing the user to feel better and more refreshed after awaking.

Many different arrangements are possible without departing from the spirit and scope of the present invention. Embodiments of the present invention are described herein with the intent to be illustrative rather than restrictive. Alternative embodiments will become apparent to those skilled in the art that do not depart from its scope. A skilled artisan may develop alternative means of implementing the disclosed improvements without departing from the scope of the present invention. Further, it will be understood that certain features and subcombinations are of utility and may be employed without reference to other features and subcombinations and are contemplated within the scope of the invention. Not all steps listed in the various figures and description need be carried out in the specific order described. The description should not be restricted to the specific described embodiments.

What is claimed is:
1. A nasal dilator, comprising:
   an internal portion comprising first and second nostril inserts; and
   an external portion comprising a connection member; wherein:

each nostril insert has a generally "C" configuration and comprises:
  a substantially vertical member;
  a first curved end extending from a first side of the substantially vertical member; and
  a second curved end extending from a second side of the substantially vertical member;
  wherein the substantially vertical member joins the first curved end to the second curved end; and
the connection member has a generally "U "configuration comprising a first leg and a second leg, wherein the first leg of the connection member is fixed to an inside face of one of the respective vertical members of the first and second nostril inserts, and the second leg of the connection member is fixed to an inside face of the other of the respective vertical members of the first and second nostril inserts, wherein the respective inside faces are inside the generally "C" configuration of the respective first and second nostril inserts, and wherein the respective vertical members of the first and second nostril inserts are substantially parallel.

2. The nasal dilator of claim 1, wherein a height of the first and second nostril inserts ranges from approximately 3 mm to approximately 10 mm.

3. The nasal dilator of claim 2, wherein a width of the first and second nostril inserts ranges from approximately 3 mm to approximately 15 mm.

4. The nasal dilator of claim 3, wherein a length of the first and second nostril inserts ranges from approximately 10 mm to approximately 25 mm.

5. The nasal dilator of claim 4, wherein a gap between the first and second nostril inserts ranges from approximately 2 to approximately 8 mm.

6. The nasal dilator of claim 5, wherein a width of the connection member ranges from approximately 5 to 15 mm.

7. The nasal dilator of claim 5, wherein the connection member is flexible to allow for temporary adjustment of the gap between the first and second nostril inserts from a first width to a second width, the temporary adjustment allowing of insertion of the nostril inserts into a user's nostrils, and wherein, subsequent to insertion, the gap returns to the first width.

8. The nasal dilator of claim 7, wherein the connection member is welded to the vertical members of the respective first and second nostril inserts.

9. The nasal dilator of claim 7, wherein the connection member is adjustably fixed to the vertical members of the respective first and second nostril inserts such that an overall height of the nasal dilator is adjustable.

10. The nasal dilator of claim 7, wherein the connection member further comprises at least one jewel or charm secured thereon.

11. The nasal dilator of claim 10, wherein the nasal dilator is coated with one of sterling silver, gold, and rose gold.

12. The nasal dilator of claim 1, further comprising a sensor for sensing at least one of the amount of oxygen entering through the nasal cavity and the amount of carbon dioxide being expelled from the nasal cavity.

13. A nasal dilator, comprising:
  an internal portion comprising first and second nostril inserts; and
  an external portion comprising a connection member;
  wherein:
    each nostril insert comprises:
      a substantially vertical member;
      a first curved end extending from a first side of the substantially vertical member;
      a second curved end extending from a second side of the substantially vertical member; and
      wherein the substantially vertical member joins the first curved end to the second curved end at one side thereof, the first and second curved ends having a gap therebetween at another side thereof; and
    the connection member comprises a first leg and a second leg, the first leg being secured to an inside face of one of the respective vertical members of the first and second nostril inserts, and the second leg being secured to an inside face of the other of the respective vertical members of the first and second nostril inserts to form the nasal dilator, whereby the respective vertical members are disposed between the first leg and the second leg of the connection member, wherein the respective vertical members are substantially parallel.

14. The nasal dilator of claim 13, wherein a height of the first and second nostril inserts ranges from approximately 3 mm to approximately 10 mm.

15. The nasal dilator of claim 14, wherein a width of the first and second nostril inserts ranges from approximately 3 mm to approximately 15 mm.

16. The nasal dilator of claim 15, wherein a length of the first and second nostril inserts ranges from approximately 10 mm to approximately 25 mm.

17. The nasal dilator of claim 16, wherein a gap between the first and second nostril inserts ranges from approximately 2 to approximately 8 mm.

18. The nasal dilator of claim 17, wherein the connection member is configured in a generally "U" shape.

19. The nasal dilator of claim 18, wherein the connection member further comprises at least one jewel or charm secured thereto.

20. The nasal dilator of claim 13, further comprising a sensor for sensing at least one of the amount of oxygen entering through the nasal cavity and the amount of carbon dioxide being expelled from the nasal cavity.

\* \* \* \* \*